US005712115A

United States Patent [19]

Hawkins et al.

[11] Patent Number: 5,712,115

[45] Date of Patent: Jan. 27, 1998

[54] HUMAN CELL DEATH-ASSOCIATED PROTEIN

[75] Inventors: Phillip R. Hawkins, Mountain View; Scott Michael Braxton, San Mateo; Lynn E. Murry, Portola Valley, all of Calif.

[73] Assignee: Incyte Pharmaceuticals, Inc., Palo Alto, Calif.

[21] Appl. No.: 618,164

[22] Filed: Mar. 19, 1996

[51] Int. Cl.$^6$ .................. C07H 21/04; C12N 15/00; C12N 15/63

[52] U.S. Cl. .............. 435/69.1; 435/320.1; 435/326; 536/23.5; 935/22; 935/66

[58] Field of Search .................. 435/69.1, 320.1, 435/240.2, 252.3, 326; 536/23.1, 23.5; 935/22, 66

[56] References Cited

PUBLICATIONS

Okura et al. (1995) Circulation 92 (8 Suppl.) I-371.
Boldin et al., A Novel Protein that Interacts with the Death Domain of Fas/APO1 Contains a Sequence Motif Related to the Death Domain, *J. Biol. Chem.*, 270:7795–7798, 1995, (GI791038).
Cleveland et al., Contenders in FasL/TNF Death Signaling, *Cell*, 81:479–482, 1995.
Chinnaiyan et al., FADD, a Novel Death Domain–Containing Protein, Interacts with the Death Domain of Fas and Initiates Apoptosis, *Cell*, 81:505–512, 1995.
Hsu et al., The TNF Receptor 1–Associated Protein TRADD Signals Cell Death and NF–kB Activation, *Cell*, 81:495–504, 1995.
Stanger, RIP: A Novel Protein Containing a Death Domain That Interacts with FAS/APO–1 (CD95) in Yeast and Causes Cell Death, *Cell*, 81:513–523, 1995.

*Primary Examiner*—Christina Y. Chan
*Assistant Examiner*—Emma Cech
*Attorney, Agent, or Firm*—Incyte Pharmaceuticals, Inc.; Lucy J. Billings; Barbara J. Luther

[57] ABSTRACT

The present invention provides a polynucleotide which identifies and encodes a human cell death-associated protein (cdap) which was isolated from a rheumatoid synovium library. The invention provides for genetically engineered expression vectors and host cells comprising a nucleic acid sequence encoding CDAP. The invention also provides for the therapeutic use of purified CDAP, cdap or its antisense molecules, or CDAP inhibitors in pharmaceutical compositions and for treatment of conditions or diseases associated with expression of CDAP. The invention also describes diagnostic assays which utilize diagnostic compositions comprising the polynucleotide, or fragments thereof, or antibodies which specifically bind to the polypeptide.

5 Claims, 5 Drawing Sheets

FIG. 1A

```
5'
     ATG GAC TTC   AGC AGA AAT   CTT TAT GAT   ATT GGG GAA   CAA CTG GAC   AGT GAA GAT
      M   D   F     S   R   N     L   Y   D     I   G   E     Q   L   D     S   E   D
                 9            18            27            36            45            54

CTG GCC TCC   CTC AAG TTC   CTG AGC CTG   GAC TAC ATT   CCG CAA AGG   AAG CAA GAA
      L   A   S     L   K   F     L   S   L     D   Y   I     P   Q   R     K   Q   E
                63            72            81            90            99           108

CCC ATC AAG   GAT GCC TTG   ATG TTA CTG   TTC CAG AGA   CTC CAG AAG   AGA ATG TTG
      P   I   K     D   A   L     M   L   L     F   Q   R     L   Q   K     R   M   L
               117           126           135           144           153           162

GAG GAA AGC   AAT CTG TCC   TTC CTG AAG   GAG CTG CAG   GAA ATT AAT   AAT AGA CTG
      E   E   S     N   L   S     F   L   K     E   L   Q     E   I   N     N   R   L
               171           180           189           198           207           216

GAT TTG CTG   ATT ACC TAC   CTA AAC ACT   AGA AAG GAG   GAA AGG ATT   AAT AGA CTT
      D   L   L     I   T   Y     L   N   T     R   K   E     E   R   I     N   R   L
               225           234           243           252           261           270

CAG ACA CCA   GGC AGG GCT   CAA ATT TCT   GCC TAC AGG   GTC ATG CTC   TAT CAG ATT
      Q   T   P     G   R   A     Q   I   S     A   Y   R     V   M   L     Y   Q   I
               279           288           297           306           315           324

TCA GAA GTG   AGC AGA TCA   GAA TTG AGG   TCT TTT AAG   TTT CTT CAA   TTG CAA GAG
      S   E   V     S   R   S     E   L   R     S   F   K     F   L   Q     L   Q   E
               333           342           351           360           369           378

GAA ATC TCC   AAA TGC AAA   CTG GAT GAT   GAC ATG AAC   CTG CTG GAT   ATT TTC ATA
      E   I   S     K   C   K     L   D   D     D   M   N     L   L   D     I   F   I
               387           396           405           414           423           432
```

```
     441         450         459     468         477         486
GAG ATG AAG AGG GTC ATC CTG GGA GAA GGA AAG TTG GAC ATC CTG AAA AGA
 E   M   K   R   V   I   L   G   E   G   K   L   D   I   L   K   R 495         504     513         522         531         540
GTC TGT GCC CAA ATC AAC AAG AGC CTG AAG ATA ATC AAC GAC TAT GAA GAA
 V   C   A   Q   I   N   K   S   L   K   I   I   N   D   Y   E   E 549         558     567         576         585         594
TTC AGC AAA GAG AGA AGC AGC CTT GAA GGA AGT CCT GAT GAA TTT TCA AAT
 F   S   K   E   R   S   S   L   E   G   S   P   D   E   F   S   N 603         612     621         630         639         648
GGG GAG GAG TTG TGT GGG GTA ATG ACA ATC TCG GAC TCT CCA AGA GAA CAG GAT
 G   E   E   L   C   G   V   M   T   I   S   D   S   P   R   E   Q   D 657         666     675         684         693         702
AGT GAA TCA CAG ACT TTG GGA CAA AGT TTA CCA AAT GAA AAG CAA ACC TCG GGG
 S   E   S   Q   T   L   G   Q   S   L   P   N   E   K   Q   T   S   G 711         720     729         738         747         756
ATA CTG TCT GAT CAT CAA CAA TCA CAA TTT TGC AAA AGC ACG GGA GAA AGT GCC
 I   L   S   D   H   Q   Q   S   Q   F   C   K   S   T   G   E   S   A 765         774
CAA ACT TCA CAG CAT TAG 3'
 Q   T   S   Q   H   *
```

```
1   ---GCAGNG--GNGTTGTTTGGGGTATTGACAAATCTCGG   n78192
1   -------GGGAGGAGTTGTGTGGGNTAATGACAA-NCTCGG   n78511
1   -------GGGAGGAGTTGTGTGGGGTAATGACAA-TCTCGG   n358257
1   CACGTNGGGAGGAGTTGTGTGGGGTAATGACAA-TCTCGG   n360192
1   CTTGAACCTTGGGAATAT-TGAGATG--GACTTCAGCAGA   n391083

36  ACTCTCCAAGAGNACAGGATAGTGANTCACAGACTTTGGA   n78192
34  ACTCTCCAAGAGAACAGGATAGTGAATCACAGACTTTGGA   n78511
34  ACTCTCCAAGAGAACAGGATAGTGNATCACAGACTTTGGA   n358257
40  ACTCTCCAAGAGAACAGGATAGTGAATCACAGACTTTGGA   n360192
38  AATCTTATGATATTGG-----GAACAC------TGGA     n391083

76  CANANTTTACCAAATGATATGCAAAACCTCGGGGCTACTA   n78192
74  CAAAGTTTACCAAATGAAAAGCAAA-CCTCGGGGATACTG   n78511
74  CAAAGTTTACCAAATGAAAAGCAAA-CCTCGGGGATACTG   n358257
80  CAAAGTTTACCAAATGAAAAGCAAA-CCTCGGGGATACTG   n360192
67  CAGTGAAGATCTGGCCTCCCTCAAGTTCCTGAG---CTG   n391083

116 AATTNANCANCAACAAATCACAANTTTTTNCAAA------  n78192
113 T-CTGATCATCAACAA-TCACAATTTTGCAAAAGCACGGG  n78511
113 T-CTGATCATCAACAA-TCACAATTTTGCAAAAGCACGGG  n358257
119 T-CTGATCATCAACAA-TCACAATTTTNCAAAAGCACGGG  n360192
104 GACT-ACATTCCGCAAA--GGAA----GCAAGAACCCATC  n391083

150 ---AAAGCNC------------------GGG--AGAAA---  n78192
151 NGNAAGTGNCCAAACTTCACAGCNTTAGGGTCAGGNNTTN  n78511
151 NGAAAGTGCCCAAACTTCACAGCATTAGGGACAGGAATGG  n358257
157 AGAAAGTGCCCAAACTTCACAGCATTAGGGACAGGAATGG  n360192
137 A-AGGATGCCTTGATGTTATTCAGAGACTCCAGGAAAAG   n391083

165 --------------AAG----TNNCCA--ACCTTTCAA    n78192
191 NTCACACTTNGATGCAGGGGNTTTGNCCACGACCTTTGAA  n78511
191 AACACACTTGGATGCAGGGGCTTTGACCACGACCTTTGAA  n358257
197 AACACACTTGGATGCAGGG                       n360192
176 AGAATG-TTGGAGGAAAGCAATCTGTCC---TTCCTGAAG  n391083
```

FIG. 3A

```
183  AA----CANT---------AA--GNGACCAGGA-----        n78192
231  GAGCTTCATTTTTGAG--NATCAA--AGNCCCACGNTTGA       n78511
231  GAGCTTCATTTT--GA--GATCAA----GCCC--------       n358257
215                                                  n360192
212  GAGCTGCTCTTCCGAATTAATAGACTGGATTTGCTGATTA       n391083

201  ----------AATAGGAAC-ACAACATTA---GGNTTN-        n78192
267  CNTGC---ACCAGTAGGAGC-AAATCNTNATNTGNNTTTT       n78511
255  -----------------------------------            n358257
215                                                  n360192
252  CCTACCTAAACACTAGAAAGGAGGAGATGGAAAGGGAACT       n391083

225  ------------------------------CAAGNG           n78192
303  TTANAAATCTACCCAACTTCATTGGNCCACNAAGTNAAC        n78511
255  ---------------------------------              n358257
215                                                  n360192
292  TCAGACAACAGGCAGGGCTCAA-ATTTCTGCCTACAGGGT       n391083

230                                                  n78192
343  CATTTT                                         n78511
255  -----T                                         n358257
215                                                  n360192
331  CA                                             n391083
```

FIG. 3B

1
HUMAN CELL DEATH-ASSOCIATED PROTEIN

FIELD OF THE INVENTION

The present invention is in the field of molecular biology; more particularly, the present invention describes the nucleic acid and amino acid sequences of a human, cell death-associated protein.

BACKGROUND OF THE INVENTION

Normal development, differentiation, and defense in multicellular organisms involves the activation and expression of genes which ultimately result in cell death. Cysteine proteases are among known molecules which carry out genetically programmed cell death. Molecules such as CPP32, apoptotic protein; Ced-3, cell death protein; and ICE, interleukin-1 B-converting enzyme are directly associated with cell destruction. These molecules are all effectors in receptor-mediated cascades which lead to cell destruction.

Lymphocyte-produced ligands activate the known cell surface receptors. Tumor necrosis factor receptor (TNFR) is induced by a growth factor, and Fas-APO receptor (FASR) which is induced by Fas ligand. The cytoplasmic portion of TNFR and FASR contain a motif known as the "death domain". The death domain which is approximately 54 residues long begins with the residues, LARQ, and ends with the residues, QMNL. Some FASRs also display a 15 residue motif known as "salvation" which associates with a protein tyrosine phosphatase and makes the cell resistant to Fas ligand. TNFR and FASR-mediated cell death usually occurs within two hours, does not require macromolecular synthesis, and may occur in the absence of a nucleus (Cleveland J L and J N Ihle (1995) Cell 81:479–482). After ligand binding, TNFR and FASR also induce sphingomy-elinases and tyrosine and serine/threonine phosphorylations.

Latent intracellular mediators are critical in cell death processes. Some of these mediators, the FADD, TRADD, RIP, and MORT1 proteins, have been cloned and characterized. They all share conserved death domains which interact with the death domain of the cell surface receptor. Once the respective death domains of the receptor and mediator have interacted, cytocidal processes are activated.

FADD is a 23.3 kD protein which interacts with FASR (Chinnaiyan A M et al. (1995) Cell 81:505–512), and TRADD is a 34 kD protein which interacts with TNFR1 (Hsu H et al. (1995) Cell 81:495–504). RIP is a 74 kD protein with an N-terminal kinase domain and a C-terminal death domain which interacts with FASR and TNFR (Stanger B Z (1995) Cell 81:513–523). MORT1 has an estimated size between 27 and 34 kD and interacts with FASR.

The experimental evidence for cell death after the association of the receptor and mediator death domains was strengthened by recent experiments in which the cloning and transient expression of death domains induced apoptosis. Where any of the death domains of either receptors or mediators were overexpressed, self-association of the death domains triggered apoptosis. Specific mutations such as the replacement of $I_{225}$ with alanine in the death domain of mouse Fas/APO1 prohibits binding of MORT1 (Boldin M P et al (1995) J Biol Chem 270:7795–7798) and prevents cell death. Similarly, introducing the cysteine protease inhibitor crmA from cowpox virus into cells transfected with mediators or their death domains prevents binding and apoptosis.

The discovery of the novel human, cell death-associated protein disclosed herein presents opportunities to study and to intercede in both normal and abnormal human cell processes. The nucleic acid sequence encoding cell death-associated protein can be used to diagnose or monitor conditions where the gene is being induced and the protein is involved in developmental, inflammatory or other disease-related processes. Induction of gene expression or delivery of the protein to metastatic cells, cancers or tumors provides a means for therapy by inducing cell death.

SUMMARY

The present invention relates to a novel human cell death associated protein whose nucleic acid sequence was identified among the polynucleotides from a human rheumatoid synovium library (SYNORAB01) and to the use of the polynucleotide (lower case, cdap) and polypeptide (upper case, CDAP) in the study, diagnosis, prevention and treatment of disease.

The novel polynucleotide encoding the cell death associated protein was first found in Incyte Clone No. 78511 through a computer generated search for nucleotide sequence alignments. The full length nucleotide sequence (SEQ ID NO:1) was assembled electronically from alignments of Incyte Clone Nos. 78192, 358257, and 360192 from SYNORAB01, and Incyte Clone No. 391083 from the T cell mixed lymphocyte reaction (TMLR2DT01) library. The coding region of the consensus molecule encodes a protein of 257 amino acids (SEQ ID NO:2). Significant features of the novel CDAP are alignment of its N terminal sequence with the MORT1 (GI 791038; Boldin et al. supra) protein associated with cell death and the presence of a leucine zipper motif.

The present invention and its use is based, in part, on the fact that CDAP, has residue similarity to the cell death proteins. Use is also based on the presence of cdap transcripts in human rheumatoid synovium and TMLR2DT01 libraries which share activated T lymphocytes.

The cdap nucleic acid sequence, oligonucleotides, fragments, portions or antisense molecules thereof, may be used in diagnostic assays of body fluids or biopsied tissues to detect expression of cdap in association with disease state. For example, cdap sequences can be used to diagnose rheumatoid arthritis, to assess tissue destruction, and to monitor the effects of treatment.

The present invention also relates, in part, to an expression vector and host cells comprising nucleic acids encoding CDAP. Such transfected host cells are useful for the production and recovery of CDAP. The present invention also encompasses purified CDAP.

The invention further provides diagnostic kits for the detection of naturally occurring CDAP and provides for the use of purified CDAP both as a positive control and to produce anti-CDAP antibodies. These antibodies may be used to monitor CDAP levels in body fluids or biopsied tissues where CDAP is expressed. The invention further provides for methods for treatment of conditions or diseases associated with expression of CDAP. These methods specifically include delivery of inhibitors to cells, tissues, or organs where CDAP is being expressed in conjunction with such conditions or diseases as AIDS, allergies including hay fever and urticaria (hives), asthma, autoimmune hemolytic anemia, ulcerative colitis, juvenile diabetes mellitus, proliferative glomerulonephritis, multiple sclerosis, myasthenia gravis, rheumatoid and osteoarthritis, scleroderma, Sjogren's syndrome, systemic lupus erythematosus, and thyroiditis.

The invention also provides pharmaceutical compositions comprising vectors containing antisense sequences which can be used in the prevention or treatment of conditions or diseases resulting from CDAP production. For example, cdap binding sequences can be introduced into adenovirus vectors and delivered to the lung by inhalation. Transfection and expression of these binding sequences can inactivate and prevent the damage caused by excessive numbers of activated T lymphocytes. Other pharmaceutical compositions such as antagonists and inhibitors can be delivered to reduce the destructive effects of activated T lymphocytes in diseases such as AIDS, allergies including hay fever and urticaria (hives), asthma, autoimmune hemolytic anemia, ulcerative colitis, juvenile diabetes mellitus, proliferative glomerulonephritis, multiple sclerosis, myasthenia gravis, rheumatoid and osteoarthritis, scleroderma, Sjogren's syndrome, systemic lupus erythematosus, and thyroiditis. Also formulated CDAP can be delivered to metastatic cells, cancers or tumors to induce apoptosis of those cells.

DESCRIPTION OF THE FIGURES

FIGS. 1A and 1B display the nucleic acid sequence (SEQ ID NO:1) and deduced amino acid sequence (SEQ ID NO:2) of cell death-associated protein (CDAP) from human rheumatoid synovium. The alignment of the nucleic acid and amino acid sequences were produced using MacDNAsis (Hitachi Software Engineering Co Ltd).

Figure 2:
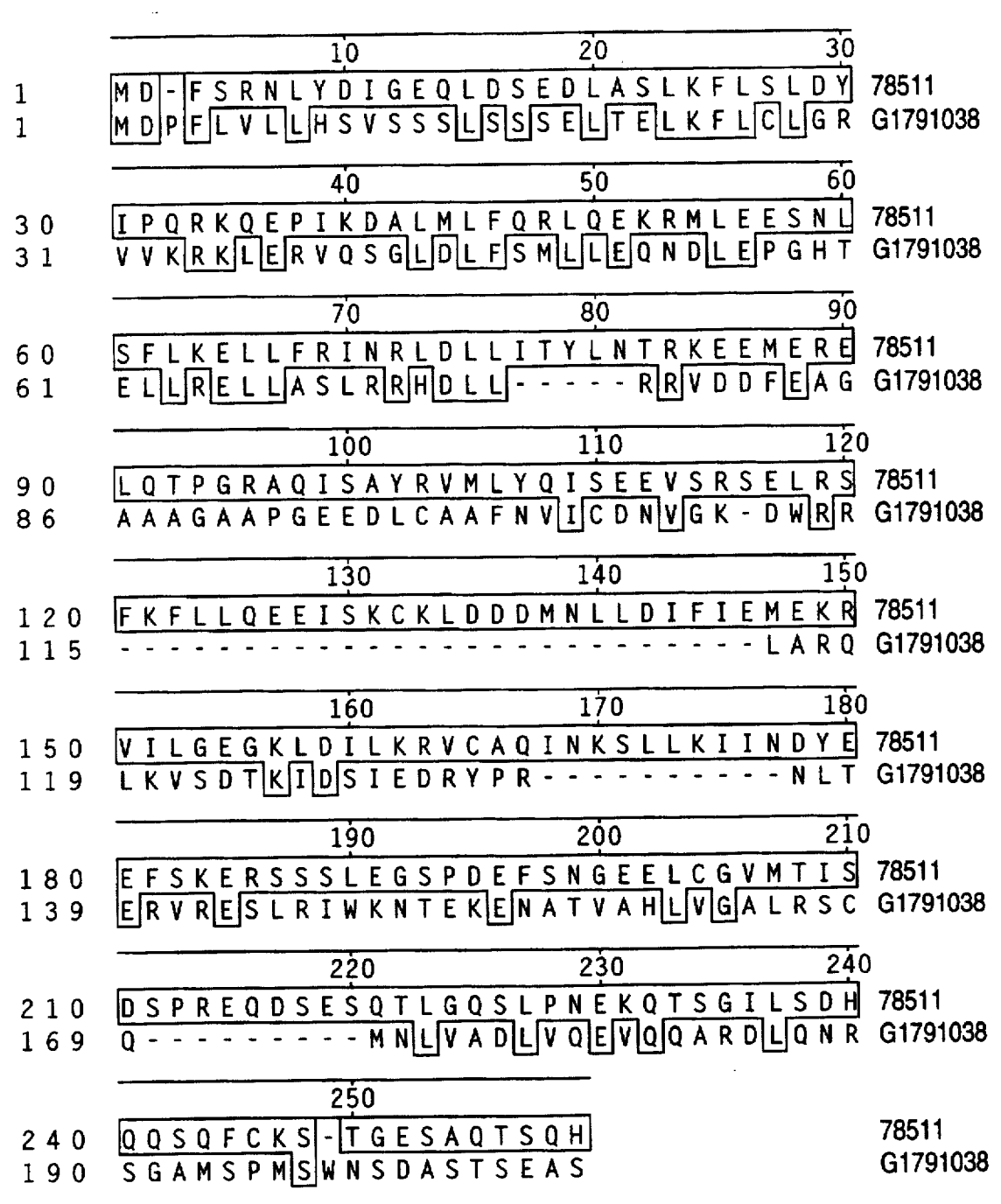

FIG. 2 shows the amino acid sequence alignment between human intracellular CDAP (SEQ ID NO:2) and GI 791038 (SEQ ID NO:3; Boldin M P et al. (1995) J Biol Chem 270:7795–98). Sequences were aligned using the multisequence alignment program of DNASTAR software.

FIGS. 3A and 3B show the nucleic acid sequence alignments among the Incyte Clone Nos. 78192 (SEQ ID NO:5), 78511 (SEQ ID NO:6), 358257 (SEQ ID NO:7), 360192 (SEQ ID NO:8), and 391083 (SEQ ID NO:9). Sequences were aligned using the multisequence alignment program of DNASTAR software (DNASTAR Inc, Madison Wis.); boxed residues show sequence identities against Incyte Clone No. 78511.

DETAILED DESCRIPTION OF THE INVENTION

The present invention relates to a novel human cell death associated protein whose nucleic acid sequence was identified among the polynucleotides from a human rheumatoid synovium library (SYNORAB01) and to the use of the polynucleotide (lower case, cdap) and polypeptide (upper case, CDAP) in the study, diagnosis, prevention and treatment of disease.

The novel polynucleotide encoding cell death associated protein was first found in Incyte Clone No. 78511 (SEQ ID NO:6) through a computer generated search for nucleotide sequence alignments. Other Incyte clones which align with at least a portion of the cdap nucleotide sequence include Incyte Clone Nos. 78192 (SEQ ID NO:5), 358257, and 360192 from SYNORAB01, and Incyte Clone No. 391083 from the T cell mixed lymphocyte reaction (TMLR2DT01) library. The consensus nucleotide sequence (SEQ ID NO:1) was assembled electronically from alignments of these molecules, and its coding region which encodes a protein of 257 amino acids (SEQ ID NO:2) was confirmed. Significant features of the novel CDAP include the presence of a leucine zipper motif, between residues $L_{42}$ and $L_{75}$ and its alignment with the N terminal sequence of the MORT1 protein (GI791038; FIG. 3) which is associated with cell death. CDAP has 76% amino acid similarity (40% identity) with the N-terminal sequence of MORT1, but it lacks the MORT1 death domain which starts at $L_{115}$ and ends at $L_{172}$. Thus, CDAP appears to be a undescribed intracellular mediator in the receptor-mediated cascade which governs apoptosis.

The present invention and its use is based, in part, on the fact that CDAP is related to the cell death protein. Use is also based on the presence of cdap transcripts in human rheumatoid synovium and TMLR2DT01 libraries which share activated T lymphocytes.

The cdap nucleic acid sequence, oligonucleotides, fragments, portions or antisense molecules thereof, may be used in diagnostic assays of body fluids or biopsied tissues to detect expression of cdap in association with disease state. For example, cdap sequences can be used to diagnose rheumatoid arthritis, to continued tissue destruction, and to monitor the return to normal function following treatment.

The present invention also relates, in part, to an expression vector and host cells comprising nucleic acids encoding CDAP. Such transfected host cells are useful for the production and recovery of CDAP. The present invention also encompasses purified CDAP.

The invention further provides diagnostic kits for the detection of naturally occurring CDAP and provides for the use of purified CDAP both as a positive control and to produce anti-CDAP antibodies. These antibodies may be used to monitor CDAP levels in body fluids or biopsied tissues where CDAP is expressed. The invention further provides for methods for treatment of conditions or diseases associated with expression of CDAP. These methods specifically include delivery of inhibitors to cells, tissues, or organs where CDAP is being expressed in conjunction with conditions or diseases such as AIDS, allergies including hay fever and urticaria (hives), asthma, autoimmune hemolytic anemia, ulcerative colitis, juvenile diabetes mellitus, proliferative glomerulonephritis, multiple sclerosis, myasthenia gravis, rheumatoid and osteoarthritis, scleroderma, Sjogren's syndrome, systemic lupus erythematosus, and thyroiditis.

The invention also provides pharmaceutical compositions comprising vectors containing antisense sequences which can be used in the prevention or treatment of conditions or diseases resulting from CDAP production. For example, cdap sequences can be introduced into adenovirus vectors and delivered to the lung by inhalation to transfect cells and produce CDAP which can inactivate and prevent the damage caused by T lymphocytes. Other pharmaceutical compositions such as formulated CDAP can be delivered to metastatic cells, cancers or tumors to provoke apoptosis of those cells.

"Nucleic acid sequence" as used herein refers to an oligonucleotide, nucleotide or polynucleotide sequence, and fragments or portions thereof, and to DNA or RNA of genomic or synthetic origin which may be single- or double-stranded, and represent the sense or antisense strand. Similarly, amino acid sequence as used herein refers to an oligopeptide, peptide, polypeptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, CDAP refers to the amino acid sequence of CDAP from any species, including bovine, ovine, porcine, equine, murine and preferably human, in a naturally occurring form or from any source whether natural, synthetic, semi-synthetic or recombinant. As used herein, "naturally occurring" refers to an amino acid sequence which is found in nature.

The present invention also encompasses CDAP variants. A preferred CDAP variant is one having at least 80% amino acid sequence similarity, a more preferred CDAP variant is one having at least 90% amino acid sequence similarity and a most preferred CDAP variant is one having at least 95% amino acid sequence similarity to the CDAP amino acid sequence (SEQ ID NO:2). A "variant" of CDAP may have an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

The term "biologically active" refers to a CDAP having structural, regulatory or biochemical functions of the naturally occurring CDAP. Likewise, "immunologically active" defines the capability of the natural, recombinant or synthetic CDAP, or any oligopeptide thereof, to induce a specific immune response in appropriate animals or cells and to bind with specific antibodies.

The term "derivative" as used herein refers to the chemical modification of a cdap or the encoded CDAP. Illustrative of such modifications would be replacement of hydrogen by an alkyl, acyl, or amino group. A CDAP derivative would encode a polypeptide which retains essential biological characteristics of natural CDAP.

As used herein, the term "purified" refers to molecules, either nucleic or amino acid sequences, that are removed from their natural environment and isolated or separated from at least one other component with which they are naturally associated.

The CDAP Coding Sequences

The nucleic acid and deduced amino acid sequences of CDAP are shown in FIGS. 1A an 1B. In accordance with the invention, any nucleic acid sequence which encodes the amino acid sequence of CDAP can be used to generate recombinant molecules which express CDAP. Relevant clones with an exact match to the nuclei acid sequence of 7811 are shown in FIGS 3A and 3B. In a specific embodiment described herein, partial sequence for cdap was first isolated among the clones from the human rheumatoid synovium library (SYNORAB01), U.S. Pat. No. 5,433,695.

Methods for DNA sequencing are well known in the art and employ such enzymes as the Klenow fragment of DNA polymerase I, Sequenase® (US Biochemical Corp, Cleveland Ohio)), Taq polymerase (Perkin Elmer), thermostable T7 polymerase (Amersham, Chicago Ill.), or combinations of recombinant polymerases and proofreading exonucleases such as the ELONGASE Amplification System marketed by Gibco BRL (Gaithersburg Md.)

Methods to extend the DNA from an oligonucleotide primer annealed to the DNA template of interest have been developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; M J Research, Watertown Mass.) and the ABI Catalyst 800 and 377 and 373 DNA sequencers (Perkin Elmer).

The quality of any particular cDNA library may be determined by performing a pilot scale analysis of the cDNAs and checking for percentages of clones containing vector, lambda or E. coli DNA, mitochondrial or repetitive DNA, and clones with exact or homologous matches to public databases.

Extending the Polynucleotide Sequence

The polynucleotide sequence of cdap may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al(1988) Nucleic Acids Res 16:8186). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker J D et al (1991; Nucleic Acids Res 19:3055–60), teach walking PCR, a method for targeted gene walking which permits retrieval of unknown sequence. Promoter-Finder™ a new kit available from Clontech (Palo Alto Calif.) uses PCR, nested primers and PromoterFinder libraries to walk in genomic DNA. This process avoids the need to screen libraries and is useful in finding intron/exon junctions.

Another PCR method, "improved Method for Obtaining Full Length cDNA Sequences" by Guegler et al, patent application Ser. No 08/487,112, filed June 7, 1995, pending, and hereby incorporated by reference, employs XL-PCR™ (Perkin Elmer) to amplify and/or extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension 5' of the promoter binding region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, cdap polynucleotide sequences which encode CDAP, fragments of the polypeptide, fusion proteins or functional equivalents thereof, may be used to generate recombinant DNA molecules that direct the expression of CDAP in appropriate host cells. Due to the inherent degeneracy of the genetic code, other DNA sequences which encode substantially the same or a functionally equivalent amino acid sequence, may be used to clone and express CDAP. As will be understood by those of skill in the art, it may be advantageous to produce CDAP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of CDAP expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of FIGS. 1A and 1B under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152, Academic Press, San Diego Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences. The term "hybridization" as used herein shall include "any process by which a strand of nucleic acid joins with a complementary strand through base pairing" (Coombs J (1994) *Dictionary of Biotechnology*, Stockton Press, New York N.Y.). Then by definition, hybridization includes the process of amplification as carried out in the polymerase chain reaction technologies described in Dieffenbach C W and G S Dveksler (1995, *PCR Primer, a Laboratory Manual*, Cold Spring Harbor Press, Plainview N.Y.) and incorporated herein by reference.

As used herein, a "deletion" is defined as a change in either nucleotide or amino acid sequence in which one or more nucleotides or amino acid residues, respectively, are absent.

As used herein, an "insertion" or "addition" is that change in a nucleotide or amino acid sequence which has resulted in the addition of one or more nucleotides or amino acid residues, respectively, as compared to the naturally occurring cdap.

As used herein, "substitution" results from the replacement of one or more nucleotides or amino acids by different nucleotides or amino acids, respectively.

Altered cdap nucleic acid sequences which may be used in accordance with the invention include deletions, insertions or substitutions of different nucleotides resulting in a polynucleotide that encodes the same or a functionally equivalent CDAP. The protein may also show deletions, insertions or substitutions of amino acid residues which produce a silent change and result in a functionally equivalent CDAP. Deliberate amino acid substitutions may be made on the basis of similarity in polarity, charge, solubility, hydrophobicity, hydrophilicity, and/or the amphipathic nature of the residues as long as the biological activity of CDAP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of cdap. As used herein, an "allele" or "allelic sequence" is an alternative form of cdap. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention may be engineered in order to alter a CDAP coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, etc.

In another embodiment of the invention, a natural, modified or recombinant cdap sequence may be ligated to a heterologous sequence to encode a fusion protein. For example, for screening of peptide libraries for inhibitors of CDAP activity, it may be useful to encode a chimeric CDAP protein expressing a heterologous epitope that is recognized by a commercially available antibody. A fusion protein may also be engineered to contain a cleavage site located between a CDAP sequence and the heterologous protein sequence, so that the CDAP may be cleaved and purified away from the heterologous moiety.

In an alternate embodiment of the invention, the coding sequence of cdap could be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize a CDAP amino acid sequence, whole or in part. For example, peptides can be synthesized by solid phase techniques, cleaved from the resin, and purified by preparative high performance liquid chromatography (eg, Creighton (1983) *Proteins Structures And Molecular Principles*, W H Freeman and Co, New York N.Y.). The composition of the synthetic peptides may be confirmed by amino acid analysis or sequencing (eg, the Edman degradation procedure; Creighton, supra)

Direct peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer. Additionally the amino acid sequence of CDAP, or any part thereof, may be altered during direct synthesis and/or combined using chemical methods with sequences from other intracellular mediators, or any part thereof, to produce a variant polypeptide.

Expression Systems

In order to express a biologically active CDAP, the nucleotide sequence encoding CDAP, or a functional equivalent, is inserted into an appropriate expression vector, ie, a vector which contains the necessary elements for the transcription and translation of the inserted coding sequence.

Methods which are well known to those skilled in the art can be used to construct expression vectors containing a CDAP coding sequence and appropriate transcriptional or translational controls. These methods include in vitro recombinant DNA techniques, synthetic techniques and in vivo recombination or genetic recombination. Such techniques are described in Maniatis et al (1989) *Molecular Cloning, A Laboratory Manual*, Cold Spring Harbor Press, Plainview N.Y. and Ausubel F M et al. (1989) *Current Protocols in Molecular Biology*, John Wiley & Sons, New York N.Y.

A variety of expression vector/host systems may be utilized to contain and express a CDAP coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of cdap, vectors based on SV40 or EBV may be used with an appropriate selectable marker.

In bacterial systems, a number of expression vectors may be selected depending upon the use intended for CDAP. For example, when large quantities of CDAP are needed for the induction of antibodies, vectors which direct high level expression of fusion proteins that are readily purified may be desirable. Such vectors include, but are not limited to, the *E. Coli* cloning and expression vector Bluescript® (Stratagene), in which the cdap coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a CDAP coding sequence may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Yearbook of Science and Technology (1992) McGraw Hill New York N.Y., pp 191–196 or Weissbach and Weissbach (1988) Methods for Plant Molecular Biology, Academic Press, New York N.Y., pp 421–463.

An alternative expression system which could be used to express cdap is an insect system. In one such system, *Autographa californica* nuclear polyhedrosis virus (AcNPV) is used as a vector to express foreign genes in *Spodoptera frugiperda* cells or in *Trichoplusia larvae*. The cdap coding sequence may be cloned into a nonessential region of the virus, such as the polyhedrin gene, and placed under control of the polyhedrin promoter. Successful insertion of cdap will render the polyhedrin gene inactive and produce recombinant virus lacking coat protein coat. The recombinant viruses are then used to infect *S. frugiperda* cells or *Trichoplusia larvae* in which CDAP is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a CDAP coding sequence may be ligated into an adenovirus transcription/translation complex consisting of the late promoter and tripartite leader sequence. Insertion in a nonessential E1 or E3 region of the viral genome will result in a viable virus capable of expressing CDAP in infected host cells. (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a cdap sequence. These signals include the ATG initiation codon and adjacent sequences. In cases where cdap, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc, have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express CDAP may be transformed using expression vectors which contain vital origins of replication or endogenous expression elements and a selectable marker gene. Following the introduction of the vector, cells may be allowed to grow for 1–2 days in an enriched media before they are switched to selective media. The purpose of the selectable marker is to confer resistance to selection and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes Calif. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the cdap is inserted within a marker gene sequence, recombinant cells containing cdap can be identified by the absence of marker gene function. Alternatively, a marker gene can be placed in tandem with a CDAP sequence under the control of a single promoter. Expression of the marker gene in response to induction or selection usually indicates expression of the tandem cdap as well.

Alternatively, host cells which contain the coding sequence for cdap and express CDAP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the cdap polynucleotide sequence can be detected by DNA-DNA or DNA-RNA hybridization or amplification using probes, portions or fragments of cdap. Nucleic acid amplification based assays involve the use of oligonucleotides or oligomers based on the cdap sequence to detect transformants containing cdap DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

CDAP can be assayed in BHK (baby hamster kidney) cells seeded on a microscope cover slip and transiently transfected with plasmid engineered to give high expression (Stanger, supra). Using a microscope and Hoescht 33258 stain, those nuclei which express CDAP appear apoptotic. Control cells transfected with a vector containing only an antibiotic resistance gene or β galactosidase appear normal. More elaborate assays such as the two-hybrid β-galactosidase expression assay are commonly used to screen for accessory molecules in the cell death pathway (Boldin, supra).

A variety of protocols for detecting and measuring the expression of CDAP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on CDAP is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to cdap include oligolabeling, nick translation, end-labeling or PCR amplification using a labeled nucleotide. Alternatively, the cdap sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of CDAP

Host cells transformed with a CDAP nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing cdap can be designed with signal sequences which direct secretion of CDAP through a particular prokaryotic or eukaryotic cell membrane. Other recombinant constructions may join cdap to nucleotide sequence encoding a polypeptide domain which will facilitate purification of soluble proteins (Kroll D J et al (1993) DNA Cell Biol 12:441–53; cf discussion of vectors infra containing fusion proteins).

CDAP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and CDAP is useful to facilitate purification.

Uses of CDAP

The rationale for diagnostic and therapeutic uses of CDAP sequences is based on the nucleic acid and amino acid sequences, their homology to MORT1, their distribution in the cDNA libraries from human rheumatoid synovium and T lymphocytes subjected to a mixed lymphocyte reaction.

The nucleic acid sequence presented in FIGS 1A and 1B, its complement, fragments or oligomers, and anti-CDAP antibodies may be used as diagnostic compositions to assay biological samples or their extracts for expression of cdap. Purified polynucleotides and polypeptides can be used as positive controls in their respective nucleic acid or protein based assays to validate and quantitate the expression of cdap. The purified nucleic acid sequences, protein, antisense molecules, antagonists or inhibitors capable of specifically binding the nucleic acid or protein can be used as pharmaceutical compositions for conditions or diseases characterized by expression of CDAP.

These compositions are useful in the diagnosis or treatment of conditions such as AIDS, allergies including hay fever and urticaria (hives), asthma, autoimmune hemolytic anemia, cancers, ulcerative colitis, juvenile diabetes mellitus, proliferative glomerulonephritis, metastatic cells, multiple sclerosis, myasthenia gravis, rheumatoid and osteoarthritis, scleroderma, Sjogren's syndrome, systemic lupus erythematosus, thyroiditis, and tumors.

The delivery of polynucleotides encoding CDAP or the protein itself, provides opportunities for early intervention in cancers. In these metastatic, tumor or cancer cells, excess CDAP induces apoptosis. On the other hand, excessive natural CDAP has been correlated with unnecessary tissue destruction in autoimmune conditions such as rheumatoid arthritis. Reducing the expression of the natural polynucleotide or neutralizing the protein can prevent joint damage. For example, transfection of chondrocytes of the rheumatoid synovium with vectors expressing antisense to cdap can provide a longer term solution than the injection of inhibitors directly into the synovial cavity.

Because CDAP is a regulatory molecule in the signalling pathway which induces apoptosis, designing a PNA which binds in the area of the leucine zipper may prevent intracellular movement or interaction with the nuclear chromatin. This, in turn, compromises the apoptotic activity of CDAP in diseases, listed above, where excessive numbers of T lymphocytes cause irreversible tissue destruction Expression and delivery of CDAP and its inhibitors for therapeutic purposes is further described under Pharmaceutical Compositions. Therapy depends on the organs or tissues involved, the specific diagnosis of the condition, and the physician to monitoring the patient's condition.

CDAP. Antibodies

Procedures well known in the art can be used for the production of antibodies to CDAP Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc., may be immunized by injection with CDAP or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to CDAP may be prepared using any technique which provides for the production of antibody molecules by continuous cell lines in culture. These include but are not limited to the hybridoma technique originally described by Koehler and Milstein (1975 Nature 256:495-497), the human B-cell hybridoma technique (Kosbor et al (1983) Immunol Today 4:72; Cote et al (1983) Proc Natl Acad Sci 80:2026-2030) and the EBV-hybridoma technique (Cole et al (1985) *Monoclonal Antibodies and Cancer Therapy*, Alan R Liss Inc, New York N.Y., pp 77-96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851-6855; Neuberger et al (1984) Nature 312:604-608; Takeda et al (1985) Nature 314:452-454). Alternatively, techniques described for the production of single chain antibodies (U.S. Pat. No. 4,946,778) can be adapted to produce CDAP-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

Antibody fragments which contain specific binding sites for CDAP may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W D et al (1989) Science 256:1275-1281).

CDAP-specific antibodies are useful for the diagnosis of conditions and diseases associated with expression of CDAP. A variety of protocols for competitive binding or immunoradiometric assays using either polyclonal or monoclonal antibodies with established specificities are well known in the art. Such immunoassays typically involve the formation of complexes between CDAP and its specific antibody and the measurement of complex formation. A two-site, monoclonal-based immunoassay utilizing monoclonal antibodies reactive to two noninterfering epitopes on a specific CDAP protein is preferred, but a competitive binding assay may also be employed. These assays are described in Maddox D E et al (1983, J Exp Med 158:1211).

Diagnostic Assays Using CDAP Specific Antibodies

Particular CDAP antibodies are useful for the diagnosis of conditions or diseases characterized by induced expression of CDAP or in assays to monitor patients being treated with CDAP. Diagnostic assays for CDAP include methods utilizing the antibody and a label to detect CDAP in human body fluids, cells, tissues or extracts of such tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring CDAP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on CDAP is preferred, but a competitive binding assay may be employed. These assays are described, among other places, in Maddox, D E et al (1983, J Exp Med 158:1211).

In order to provide a basis for the diagnosis of disease, normal or standard values for CDAP expression must be established. This is accomplished by combining body fluids or cell extracts taken from normal subjects, either animal or human, with antibody to CDAP under conditions suitable for complex formation which are well known in the art. The amount of standard complex formation may be quantified by comparing it with a dilution series of positive controls where a known amount of antibody is combined with known concentrations of purified CDAP. Then, standard values obtained from normal samples may be compared with values obtained from sample from subjects potentially affected by a disorder or disease related to CDAP expression. Deviation between standard and subject values establishes the presence of disease state.

Drug Screening

CDAP, its catalytic or immunogenic fragments or oligopeptides can be used for screening therapeutic compounds in any of a variety of drug screening techniques. The fragment employed in such a test may be free in solution, affixed to a solid support, borne on a cell surface, or located intracellularly. The decrease of catalytic activity or the formation of binding complexes, between CDAP and the agent being tested, may be measured.

Another technique for drug screening which provides for high throughput screening of compounds having suitable binding affinity to the CDAP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of CDAP and washed. Bound CDAP is then detected by methods well known in the art. Purified CDAP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding CDAP specifically compete with a test compound for binding CDAP. In this manner, the antibodies can be used to detect the presence of any peptide which shares one or more antigenic determinants with CDAP.

Uses of the Polynucleotide Encoding CDAP

A polynucleotide, cdap, or any part thereof, may be used for diagnostic and/or therapeutic purposes. For diagnostic purposes, the cdap of this invention may be used to detect and quantitate gene expression in conditions or diseases in which CDAP activity may be implicated. These specifically include, but are not limited to, activation of T lymphocytes in diseases such as AIDS, allergies including hay fever and urticaria (hives), asthma, autoimmune hemolytic anemia, ulcerative colitis, juvenile diabetes mellitus, proliferative glomerulonephritis, multiple sclerosis, myasthenia gravis, rheumatoid and osteoarthritis, scleroderma, Sjogren's syndrome, systemic lupus erythematosus, and thyroiditis, particularly in tissues with endocrine production or response. Included in the scope of the invention are oligonucleotide sequences, antisense RNA and DNA molecules, PNAs and ribozymes, which inhibit translation of a cdap.

Another aspect of the subject invention is to provide for hybridization or PCR probes which are capable of detecting polynucleotide sequences, including genomic sequences, encoding CDAP or closely related molecules. The specificity of the probe, whether it is made from a highly conserved region, eg, 10 unique nucleotides in the 5' regulatory region, or a less conserved region, eg, between cysteine residues especially in the 3' region, and the stringency of the hybridization or amplification (high, intermediate or low) will determine whether the probe identifies only naturally occurring cdap or related sequences.

Diagnostics

Polynucleotide sequences encoding CDAP may be used for the diagnosis of conditions or diseases or monitoring treatment of conditions or diseases where the expression of CDAP causes wasting or apoptosis. For example, polynucleotide sequences encoding CDAP may be used in hybridization or PCR assays of fluids or tissues from biopsies to detect cdap expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for cdap expression must be established. This is accomplished by combining body fluids or cell extracts taken from normal subjects, either animal or human, with cdap or a portion thereof, under conditions suitable for hybridization or amplification. Standard hybridization may be quantified by comparing the values obtained for normal subjects with a dilution series of positive controls run in the same experiment where a known amount of purified cdap is used. Standard values obtained from normal samples may be compared with values obtained from samples from subjects potentially affected by a disorder or disease related to cdap expression. Deviation between standard and subject values establishes the presence of a particular condition or disease state.

If disease is established, an existing therapeutic agent is administered, and a treatment profile may be generated. Finally, the assay may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the cdap sequence. Such oligomers are generally chemically synthesized, but they may be generated enzymatically or produced from a recombinant source. Oligomers generally comprise two nucleotide sequences, one with sense orientation (5'–>3') and one with antisense (3'<–5') employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, increased amounts of cdap in fluid removed from a rheumatoid synovium may indicate the presence of activated lymphocytes and progressive tissue destruction. A definitive diagnosis of this type may allow health professionals to treat the patient and prevent further worsening of the condition. Similarly, assays known to those of skill in the art can be used to monitor the progress of a patient displaying a cdap associated disease state during treatment.

Therapeutics

The polynucleotide disclosed herein may be useful in the treatment of various conditions or diseases. By introducing the cdap sequence into cancerous cells, gene therapy can be used to shrink or eradicate metastatic cells, cancers or tumors. In such instances, the expression of the introduced cdap induces apoptosis.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express CDAP. See, for example, the techniques described in Maniatis et al (supra) and Ausubel et al(supra).

The polynucleotides comprising full length cDNA sequence and/or its regulatory elements enable researchers to use cdap as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding CDAP can be turned off by transfecting a cell or tissue with expression vectors which express high levels of a cdap fragment. Such constructs can flood cells with untranslatable sense or antisense sequences. Even in the absence of integration into the DNA, such vectors may continue to transcribe RNA molecules until all copies are disabled by endogenous nucleases. Such transient expression may last for a month or more with a non-replicating vector (Mettler I, personal communication) and even longer if appropriate replication elements are part of the vector system.

On the other hand, stable transformation of appropriate germ line cells, or preferably a zygote, with a vector containing antisense fragments may produce a transgenic organism (U.S. Pat. No. 4,736,866, 12 Apr. 1988), with a significantly compromised naturally occurring cdap gene.

As mentioned above, modifications of gene expression can be obtained by designing antisense molecules, DNA, RNA or PNA, to the control regions of cdap, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al. (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of cdap.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding CDAP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference.

Furthermore, the nucleotide sequences for cdap disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for cdap can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al. (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention comprises pharmaceutical compositions which may comprise antibodies, antagonists, or inhibitors of CDAP, alone or in combination with at least one other agent, such as stabilizing compound, which may be administered in any sterile, biocompatible pharmaceutical carrier, including, but not limited to, saline, buffered saline, dextrose, and water. CDAP or its inhibitors can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Further details on techniques for formulation and administration may be found in the latest edition of "Remington's Pharmaceutical Sciences" (Maack Publishing Co, Easton Pa). Although local delivery is desirable, there are other means, for example, oral administration or parenteral delivery, including intra-arterial (directly to the tumor), intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks's solution, Ringer's solution, or physiologically buffered saline. For topical administration, penetrants appropriate to the particular barrier to be permeated are used in the formulation. Such penetrants are generally known in the art.

The pharmaceutical compositions can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. The determination of an effective dose is well within the capability of those skilled in the art, especially in light of the disclosure provided below.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, eg, by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For administration of CDAP, such labeling would include amount, frequency and method of administration.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays, eg, of neoplastic cells. Then, preferably, dosage can be formulated in animal models affected with the neoplasm to achieve a desirable concentration range and route of administration. Such information can be used to determine useful doses and route of administration in humans.

A therapeutically effective dose refers to that amount of CDAP or inhibitors of CDAP which ameliorates the symptoms or condition. Toxicity and therapeutic efficacy of such compounds can be determined by standard pharmaceutical procedures in cell cultures or experimental animals, eg, for determining the LD50 (the dose lethal to 50% of the population) and the ED50 (the dose therapeutically effective in 50% of the population). The dose ratio between toxic and therapeutic effects is the therapeutic index, and it can be expressed as the ratio ED50/LD50. Compounds, CDAP variants or fragments, which exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. No. 4,657,760; 5,206,344; or 5,225,212. Those skilled in the art will employ different formulations for antisense molecules than for the inhibitors of CDAP. Similarly, delivery of polynucleotides or polypeptides to cancerous cells will be specific to the cells, condition, location, etc.

It is contemplated CDAP can be expressed or delivered to eradicate metastatic cells, cancers or tumors, and that conditions or diseases in which the expression of CDAP are implicated can be treated with either antisense, PNA molecules, antagonists or inhibitors of CDAP. The timing of and amount of CDAP expression is implicated in conditions and diseases such as AIDS, allergies including hay fever and urticaria (hives), asthma, autoimmune hemolytic anemia, ulcerative colitis, juvenile diabetes mellitus, proliferative glomerulonephritis, multiple sclerosis, myasthenia gravis, rheumatoid and osteoarthritis, scleroderma, Sjogren's syndrome, systemic lupus erythematosus, and thyroiditis. The assays previously described may be used to diagnose these conditions and to monitor efficacy of treatment.

The examples below are provided to illustrate the subject invention. These examples are provided by way of illustration and are not included for the purpose of limiting the invention.

EXAMPLES

I SYNORAB01 cDNA Library Construction

The SYNORAB01 cDNA library was constructed from RNA isolated from hip synovial tissue removed from a 68 year old Caucasian with rheumatoid arthritis during hip replacement surgery. The frozen tissue was ground in a mortar and pestle and lysed immediately in a buffer containing guanidinium isothiocyanate. The lysate was extracted with acid phenol and centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was precipitated using 0.3M sodium acetate and 2.5 volumes of ethanol, resuspended in water and DNase treated for 15 min at 37° C. The RNA was isolated using the Qiagen Oligotex kit (QIAGEN Inc, Chatsworth Calif.) and used to construct the cDNA library.

cDNA synthesis was primed using a combination of oligo d(T) and random primers, and synthetic adaptor oligonucleotides were ligated onto the cDNA ends to enable insertion into the Uni-ZAP™ vector system (Stratagene). E. coli host strain XL1-Blue® (Stratagene) was co-transfected with phagemid and f1 helper phage particles. Proteins derived from both the lambda phage and f1 helper phage initiated new DNA synthesis from defined sequences on the lambda target DNA to create the smaller, single-stranded circular pBluescript® phagemid (Stratagene) which contains the SYNORAB01 inserts. When the phagemid DNA was released from the cells, it was purified and used to reinfect fresh bacterial host cells (SOLR™; Stratagene). Transformed bacteria expressing the β-lactamase gene on the phagemid survived selection on medium containing ampicillin and produced double-stranded phagemid.

II Isolation and Sequencing of cDNA Clones

Following the recommended protocols, phagemid DNA was purified using the QIAWELL-8 Plasmid Purification System (QIAGEN Inc, Chatsworth Calif.)and prepared for sequencing. The cDNA inserts from random isolates of the pituitary library were sequenced by the method of Sanger F and A R Coulson (1975; J Mol Biol 94:441f). Methods for DNA sequencing are well known in the art and use DNA polymerase Klenow fragment, SEQUENASE™ (US Biochemical Corp., Cleveland Ohio) or Taq polymerase to extend DNA chains from an oligonucleotide primer annealed to the DNA template of interest. Methods have been developed to sequence both single- and double-stranded templates.

Chain termination reaction products were electrophoresed on urea-polyacrylamide gels and detected by fluorescence. The SYNORAB01 cDNAs were prepared and sequenced using the ABI Catalyst 800 and 373 DNA sequencers (Perkin Elmer).

III Homology Searching of cDNA Clones and Their Deduced Proteins

Each cDNA was compared to sequences in GenBank using a search algorithm incorporated into the ABI INHERIT™ 670 Sequence Analysis System (Perkin Elmer). In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Extension of the Polynucleotide Sequence to Recover Regulatory Elements

The nucleic acid sequence of full length cdap (SEQ ID NO:1) may be used to design oligonucleotide primers for obtaining 5' sequences from genomic libraries. One primer is synthesized to initiate extension in the antisense direction (XLR) and the other is synthesized to extend sequence in the sense direction (XLF). The primers allowed the known cdap sequence to be extended "outward" generating amplicons containing new, unknown nucleotide sequence for the control region of interest. The initial primers may be designed from the cDNA using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

A human genomic library is used to extend and amplify 5' upstream sequence. If necessary, a second set of primers is designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M J Research, Watertown Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (L B)-agar (Sambrook J et al, supra) containing 2× Carb. The following day, several colonies are randomly picked from each plate and cultured in 150 µl of liquid LB/2× carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ ID NO:1 may be employed to screen cDNAs, mRNAs or genomic DNAs. Although the labeling of oligonucleotides, consisting of about 20 base-pairs, is specifically described, essentially the same procedure may be used with larger cDNA fragments. Oligonucleotides are labeled by combining 50 pmol of each oligomer and 250 mCi of [$\gamma$—$^{32}$P] adenosine triphosphate (Amersham, Chicago Ill.) and T4 polynucleotide kinase (DuPont NEN®, Boston Mass.). The labeled oligonucleotides are purified with Sephadex G-25 super fine resin column (Pharmacia). A portion containing $10^7$ counts per minute of each is used in a typical membrane based hybridization analysis of human genomic DNA digested with one of the following endonucleases (Ase I, Bgl II, EcoR I, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VI Antisense Molecules

The cdap sequence, or any part thereof, provides the basis for the design of antisense molecules which may be used to inhibit in vivo expression of naturally occurring cdap. Although use of antisense oligomers, consisting of about 20 base-pairs, is specifically described, essentially the same procedure may be used with larger or smaller nucleic acid fragments. A complementary oligonucleotide based on the untranslated leader or the coding sequence of cdap may be used to inhibit expression of naturally occurring cdap. The complementary oligonucleotide is designed to inhibit transcription by preventing promoter binding or translation of a cdap transcript by preventing the ribosomal binding.

VII Expression of CDAP

Expression of the CDAP may be accomplished by subcloning the cDNAs into appropriate vectors and transfecting the vectors into host cells. The pBluescript vector used for cloning, is used to express CDAP in *E. coli.*, strain XL1-BlueMRF™ (Stratagene). Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length CDAP. A signal sequence may be added to direct the secretion of CDAP into the bacterial growth media for easier purification.

VIII CDAP Activity

CDAP is assayed in BHK cells seeded on a microscope cover slip and transiently transfected with a plasmid containing the gene for β galactosidase, into which cdap has been engineered. The cells are fixed after twelve hours and incubated in a buffer containing X-gal to visualize β galactosidase activity. Using a microscope and Hoescht 33258 stain, the nuclei expressing CDAP appear apoptotic: the affected cells show loss of adherence, are intensely blue and shrunken, and exhibit membrane blebbing. Control cells are transfected with vector only and show cytoplasmic staining and normal nuclei. This technique has been fully described in Stanger (supra), incorporated herein by reference.

IX Production of CDAP Specific Antibodies

Although CDAP purified using PAGE electrophoresis (Maniatis, supra) are used to immunize rabbits using standard protocols, a monoclonal approach is more easily employed. The amino acid sequence translated from CDAP is analyzed using DNASTAR software (DNASTAR Inc) to determine regions of high immunogenicity and a corresponding oligopeptide is synthesized and used to raise antibodies by means known to those of skill in the art. Analysis to select appropriate epitopes, such as those near the C-terminus or in adjacent hydrophilic regions is described by Ausubel F M et al (supra).

Typically, the oligopeptides are 15 residues in length, synthesized using an ABI Peptide Synthesizer Model 431A (Perkin Elmer) using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

X Purification of Naturally occurring CDAP Using Specific Antibodies

Naturally occurring or recombinant CDAP is purified by immunoaffinity chromatography using antibodies specific for CDAP. An immunoaffinity column is constructed by covalently coupling CDAP antibody to an activated chromatographic resin such as CnBr-activated Sepharose (Pharmacia Biotech). After the coupling, the resin is blocked and washed according to the manufacturer's instructions.

Media containing CDAP is passed over the immunoaffinity column, and the column is washed under conditions that allow the preferential absorbance of CDAP (eg, high ionic strength buffers in the presence of detergent). The column is eluted under conditions that disrupt antibody/CDAP binding (eg, a buffer of pH 2–3 or a high concentration of a chaotrope such as urea or thiocyanate ion), and CDAP is collected.

XI Identification of Molecules Which Interact with CDAP

CDAP, or biologically active fragments thereof, is labeled with $^{125}$I Bolton-Hunter reagent (Bolton, A E and Hunter, W M (1973) Biochem J 133: 529). Candidate molecules previously arrayed in the wells of a 96 well plate are incubated with the labeled CDAP, washed and any wells with labeled CDAP complex are assayed. Data obtained using different concentrations of CDAP are used to calculate values for the number, affinity, and association of CDAP with the candidate inhibitory molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A purified polynucleotide encoding a polypeptide consisting of the amino acid sequence shown in SEQ ID NO:2.

2. The polynucleotide of claim 1 wherein the nucleic acid sequence consists of SEQ ID NO:1, or its complement.

3. An expression vector comprising the polynucleotide of claim 1.

4. A host cell transformed with the expression vector of claim 3.

5. A method for producing a polypeptide consisting of the amino acid sequence shown in SEQ ID NO:2, the method comprising the steps of:

a) culturing the host cell of claim 4 under conditions suitable for the expression of the polypeptide, and b) recovering the polypeptide from the host cell culture.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 2322 base pairs
( B ) TYPE: nucleic acid ( C ) STRANDEDNESS: single
( D ) TOPOLOGY: linear ( i i ) MOLECULE TYPE: cDNA ( v i i ) IMMEDIATE SOURCE:
( A ) LIBRARY: RHEUMATOID SYNOVIUM
( B ) CLONE: 78511

( x i ) SEQUENCE DESCRIPTION: SEQ ID NO:1:

| | | | | | |
|---|---|---|---|---|---|
| CTTGAACCTT | GGGAATATTG | AGATGGACTT | CAGCAGAAAT | CTTTATGATA | TTGGGGAACA | 60 |
| ACTGGACAGT | GAAGATCTGG | CCTCCCTCAA | GTTCCTGAGC | CTGGACTACA | TTCCGCAAAG | 120 |
| GAAGCAAGAA | CCCATCAAGG | ATGCCTTGAT | GTTATTCCAG | AGACTCCAGG | AAAAGAGAAT | 180 |
| GTTGGAGGAA | AGCAATCTGT | CCTTCCTGAA | GGAGCTGCTC | TTCCGAATTA | ATAGACTGGA | 240 |
| TTTGCTGATT | ACCTACCTAA | ACACTAGAAA | GGAGGAGATG | GAAAGGGAAC | TTCAGACACC | 300 |
| AGGCAGGGCT | CAAATTTCTG | CCTACAGGGT | CATGCTCTAT | CAGATTTCAG | AAGAAGTGAG | 360 |
| CAGATCAGAA | TTGAGGTCTT | TTAAGTTTCT | TTGCAAGAG | GAAATCTCCA | AATGCAAACT | 420 |
| GGATGATGAC | ATGAACCTGC | TGGATATTTT | CATAGAGATG | GAGAAGAGGG | TCATCCTGGG | 480 |
| AGAAGGAAAG | TTGGACATCC | TGAAAAGAGT | CTGTGCCCAA | ATCAACAAGA | GCCTGCTGAA | 540 |
| GATAATCAAC | GACTATGAAG | AATTCAGCAA | AGAGAGAAGC | AGCAGCCTTG | AAGGAAGTCC | 600 |
| TGATGAATTT | TCAAATGGGG | AGGAGTTGTG | TGGGGTAATG | ACAATCTCGG | ACTCTCCAAG | 660 |
| AGAACAGGAT | AGTGAATCAC | AGACTTTGGG | ACAAAGTTTA | CCAAATGAAA | AGCAAACCTC | 720 |
| GGGGATACTG | TCTGATCATC | AACAATCACA | ATTTTGCAAA | AGCACGGGAG | AAAGTGCCCA | 780 |
| AACTTCACAG | CATTAGGGAC | AGGAATGGAA | CACACTTGGA | TGCAGGTACA | GTAGAACCCA | 840 |
| AAAGAGAAAA | GTAAAATATT | TCTTATGCCT | ATTTTTTTT | AAATCAAAAG | GGAGAGAACA | 900 |
| AAAGCTATAC | CAAAAGGGCC | ATGTTTCAAG | AAAATGGATT | TAAACATATT | TCCCTGTGGA | 960 |
| GGGGCTTTGA | CCACGACCTT | TGAAGAGCTT | CATTTGAGA | TCAAGCCCCA | CCATGACTGC | 1020 |
| ACAGTAGAGC | AAATCTATGA | GATTTTGAAA | ATCTACCAAC | TCATGGACCA | CAGTAACATG | 1080 |
| GACTGCTTCA | TCTGCTGTAT | CCTCTCCCAT | GGGAGACAAG | GGCATCATCT | ATGGCACTGA | 1140 |
| TGGACAGGAG | GCCCCCATCT | ATGAGCTGAC | ATCTCAGTTC | ACTGGTTTGA | AGTGCCCTTC | 1200 |
| CCTTGCTGGA | AAACCCAAAG | TGTTTTTTAT | TCAGGCTTGT | CAGGGGATA | ACTACCAGAA | 1260 |
| AGGTATACCT | GTTGAGACTG | ATTCAGAGGA | GCAACCCTAT | TTAGAAATGG | ATTTATCATC | 1320 |
| ACCTCAAACG | AGATATATCC | CGGATGAGGC | TGACTTTCTG | CTGGGGATGG | CCACTGTGAA | 1380 |
| TAACTGTGTT | TCCTACCGAA | ACCCTGCAGA | GGGAACCTGG | TACATCCAGT | CACTTTGCCA | 1440 |
| GAGCCTGAGA | GAGCGATGTC | CTCGAGGCGA | TGATATTCTC | ACCATCCTGA | CTGAAGTGAA | 1500 |
| CTATGAAGTA | AGCAACAAGG | ATGACAAGAA | AAACATGGGG | AAACAGATGC | CTCAGCCTAC | 1560 |
| TTTCACACTA | AGAAAAAAAC | TTGTCTTCCC | TTCTGATTGA | TGGTGCTATT | TTGTTTGTTT | 1620 |
| TGTTTGTTT | TGTTTTTTG | AGACGGATCT | CGCTCTGTCG | CCCAGGCTGG | AGTGCAGTGG | 1680 |
| CGTGATCTCG | GCTCACCGCA | AGCTCCGCTC | CCGGGTTCAC | GCCATTCTCC | TGCCTCAGCC | 1740 |
| TCCCGAGTAG | CTGGGACTAC | AGGGCCCGC | CACCACACCT | GGCTAATTTT | TTAAAAATAT | 1800 |
| TTTAGTAGA | GACAGGGTTT | CACTGTGTTA | GCCAGGGTGG | TCTTGATCTC | CTGACCTCGT | 1860 |
| GATCCACCCA | GCACTTGGG | AGGTTGAGGT | GGGAGGATTG | CTTGAACCCA | AGAGGTCAAG | 1920 |
| GCTGCAGTGA | GCCATGTTCA | CGCCGCTGCA | CTCAAGCTTG | GGTGACAGAG | CAAGACCCCG | 1980 |
| TCTCAAAAAA | AATTTTTTTT | TTAATAAAAC | AAAATTTGTT | TGAAATCTTT | TAAAAATTCA | 2040 |
| AATGATTTTT | ACAAGTTTTA | AATAAGCTCT | CCCCAAACTT | GCTTTATGCC | TTCTTATTGC | 2100 |

```
TTTTATGATA TATATATGCT TGGCTAACTA TATTTGCTTT TTGCTAACAA TGCTCTGGGG    2160

TCTTTTTATG CATTTGCATT TGCTCTTTCA TCTCTGCTTG GATTATTTTA AATCATTAGG    2220

AATTAAGTTA TCTTTAAAAT TTAAGTATCT TTTTTCAAAA ACATTTTTTA ATAGAATAAA    2280

ATATAATTTG ATCTTAAAAA AAAAAAAAA  AAAAAACTCG AG                       2322
```

( 2 ) INFORMATION FOR SEQ ID NO:2:

( i ) SEQUENCE CHARACTERISTICS:
        ( A ) LENGTH: 257 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: RHEUMATOID SYNOVIUM
        ( B ) CLONE: 78511

( x i ) SEQUENCE DESCRIPTION: SEQ ID NO:2:

```
Met Asp Phe Ser Arg Asn Leu Tyr Asp Ile Gly Glu Gln Leu Asp Ser
 1               5                  10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Gly Gln
    210                 215                 220

Ser Leu Pro Asn Glu Lys Gln Thr Ser Gly Ile Leu Ser Asp His Gln
225                 230                 235                 240

Gln Ser Gln Phe Cys Lys Ser Thr Gly Glu Ser Ala Gln Thr Ser Gln
                245                 250                 255

His
```

( 2 ) INFORMATION FOR SEQ ID NO:3:

( i ) SEQUENCE CHARACTERISTICS:

(A) LENGTH: 208 amino acids
(B) TYPE: amino acid
(C) STRANDEDNESS: single
(D) TOPOLOGY: linear (ii) MOLECULE TYPE: peptide (vii) IMMEDIATE SOURCE:
(A) LIBRARY: GENBANK
(B) CLONE: 791038

(xi) SEQUENCE DESCRIPTION: SEQ ID NO:3:

| Met | Asp | Pro | Phe | Leu | Val | Leu | Leu | His | Ser | Val | Ser | Ser | Ser | Leu | Ser |
|---|---|---|---|---|---|---|---|---|---|---|---|---|---|---|---|
| 1 | | | | 5 | | | | | 10 | | | | | 15 | |

| Ser | Ser | Glu | Leu | Thr | Glu | Leu | Lys | Phe | Leu | Cys | Leu | Gly | Arg | Val | Val |
|---|---|---|---|---|---|---|---|---|---|---|---|---|---|---|---|
| | | | | 20 | | | | 25 | | | | | 30 | | |

| Lys | Arg | Lys | Leu | Glu | Arg | Val | Gln | Ser | Gly | Leu | Asp | Leu | Phe | Ser | Met |
|---|---|---|---|---|---|---|---|---|---|---|---|---|---|---|---|
| | | 35 | | | | | 40 | | | | | 45 | | | |

| Leu | Leu | Glu | Gln | Asn | Asp | Leu | Glu | Pro | Gly | His | Thr | Glu | Leu | Leu | Arg |
|---|---|---|---|---|---|---|---|---|---|---|---|---|---|---|---|
| | 50 | | | | | 55 | | | | | 60 | | | | |

| Glu | Leu | Leu | Ala | Ser | Leu | Arg | Arg | His | Asp | Leu | Leu | Arg | Arg | Val | Asp |
|---|---|---|---|---|---|---|---|---|---|---|---|---|---|---|---|
| 65 | | | | | 70 | | | | | 75 | | | | | 80 |

| Asp | Phe | Glu | Ala | Gly | Ala | Ala | Ala | Gly | Ala | Ala | Pro | Gly | Glu | Glu | Asp |
|---|---|---|---|---|---|---|---|---|---|---|---|---|---|---|---|
| | | | | 85 | | | | | 90 | | | | | 95 | |

| Leu | Cys | Ala | Ala | Phe | Asn | Val | Ile | Cys | Asp | Asn | Val | Gly | Lys | Asp | Trp |
|---|---|---|---|---|---|---|---|---|---|---|---|---|---|---|---|
| | | | 100 | | | | | 105 | | | | | 110 | | |

| Arg | Arg | Leu | Ala | Arg | Gln | Leu | Lys | Val | Ser | Asp | Thr | Lys | Ile | Asp | Ser |
|---|---|---|---|---|---|---|---|---|---|---|---|---|---|---|---|
| | | 115 | | | | | 120 | | | | | 125 | | | |

| Ile | Glu | Asp | Arg | Tyr | Pro | Arg | Asn | Leu | Thr | Glu | Arg | Val | Arg | Glu | Ser |
|---|---|---|---|---|---|---|---|---|---|---|---|---|---|---|---|
| | 130 | | | | | 135 | | | | | 140 | | | | |

| Leu | Arg | Ile | Trp | Lys | Asn | Thr | Glu | Lys | Glu | Asn | Ala | Thr | Val | Ala | His |
|---|---|---|---|---|---|---|---|---|---|---|---|---|---|---|---|
| 145 | | | | | 150 | | | | | 155 | | | | | 160 |

| Leu | Val | Gly | Ala | Leu | Arg | Ser | Cys | Gln | Met | Asn | Leu | Val | Ala | Asp | Leu |
|---|---|---|---|---|---|---|---|---|---|---|---|---|---|---|---|
| | | | | 165 | | | | | 170 | | | | | 175 | |

| Val | Gln | Glu | Val | Gln | Gln | Ala | Arg | Asp | Leu | Gln | Asn | Arg | Ser | Gly | Ala |
|---|---|---|---|---|---|---|---|---|---|---|---|---|---|---|---|
| | | | 180 | | | | | 185 | | | | | 190 | | |

| Met | Ser | Pro | Met | Ser | Trp | Asn | Ser | Asp | Ala | Ser | Thr | Ser | Glu | Ala | Ser |
|---|---|---|---|---|---|---|---|---|---|---|---|---|---|---|---|
| | | 195 | | | | | 200 | | | | | 205 | | | |

(2) INFORMATION FOR SEQ ID NO:4:

(i) SEQUENCE CHARACTERISTICS:
(A) LENGTH: 230 base pairs
(B) TYPE: nucleic acid
(C) STRANDEDNESS: single
(D) TOPOLOGY: linear (ii) MOLECULE TYPE: cDNA (vii) IMMEDIATE SOURCE:
(A) LIBRARY: RHEUMATOID SYNOVIUM
(B) CLONE: 78192

(xi) SEQUENCE DESCRIPTION: SEQ ID NO:4:

```
GCAGNGGNGT TGTTTGGGGT ATTGACAAAT CTCGGACTCT CCAAGAGNAC AGGATAGTGA     60
NTCACAGACT TTGGACANAN TTTACCAAAT GATATGCAAA ACCTCGGGGC TACTAAATTN   120
ANCANCAACA AATCACAANT TTTTNCAAAA AAGCNCGGGA GAAAAAGTNN CCAACCTTTC   180
AAAACANTAA GNGACCAGGA AATAGGAACA CAACATTAGG NTTNCAAGNG              230
```

(2) INFORMATION FOR SEQ ID NO:5:

( i ) SEQUENCE CHARACTERISTICS:
    ( A ) LENGTH: 348 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: RHEUMATOID SYNOVIUM
    ( B ) CLONE: 78511

( x i ) SEQUENCE DESCRIPTION: SEQ ID NO:5:

| | | | | | |
|---|---|---|---|---|---|
| GGGAGGAGTT | GTGTGGGNTA | ATGACAANCT | CGGACTCTCC | AAGAGAACAG | GATAGTGAAT | 60
| CACAGACTTT | GGACAAAGTT | TACCAAATGA | AAAGCAAACC | TCGGGGATAC | TGTCTGATCA | 120
| TCAACAATCA | CAATTTTGCA | AAAGCACGGG | NGNAAGTGNC | CAAACTTCAC | AGCNTTAGGG | 180
| TCAGGNNTTN | NTCACACTTN | GATGCAGGGG | NTTGNCCAC | GACCTTTGAA | GAGCTTCATT | 240
| TTTGAGNATC | AAAGNCCCAC | GNTTGACNTG | CACCAGTAGG | AGCAAATCNT | NATNTGNNTT | 300
| TTTTANAAAT | CTACCCAACT | TCATTGGNCC | CACNAAGTNA | ACCATTTT | | 348

( 2 ) INFORMATION FOR SEQ ID NO:6:

( i ) SEQUENCE CHARACTERISTICS:
    ( A ) LENGTH: 255 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: RHEUMATOID SYNOVIUM
    ( B ) CLONE: 358257

( x i ) SEQUENCE DESCRIPTION: SEQ ID NO:6:

| | | | | | |
|---|---|---|---|---|---|
| GGGAGGAGTT | GTGTGGGGTA | ATGACAATCT | CGGACTCTCC | AAGAGAACAG | GATAGTGNAT | 60
| CACAGACTTT | GGACAAAGTT | TACCAAATGA | AAAGCAAACC | TCGGGGATAC | TGTCTGATCA | 120
| TCAACAATCA | CAATTTTGCA | AAAGCACGGG | NGAAAGTGCC | CAAACTTCAC | AGCATTAGGG | 180
| ACAGGAATGG | AACACACTTG | GATGCAGGGG | CTTTGACCAC | GACCTTTGAA | GAGCTTCATT | 240
| TTGAGATCAA | GCCCT | | | | | 255

( 2 ) INFORMATION FOR SEQ ID NO:7:

( i ) SEQUENCE CHARACTERISTICS:
    ( A ) LENGTH: 215 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: RHEUMATOID SYNOVIUM
    ( B ) CLONE: 360192

( x i ) SEQUENCE DESCRIPTION: SEQ ID NO:7:

| | | | | | |
|---|---|---|---|---|---|
| CACGTNGGGA | GGAGTTGTGT | GGGGTAATGA | CAATCTCGGA | CTCTCCAAGA | GAACAGGATA | 60
| GTGAATCACA | GACTTTGGAC | AAAGTTTACC | AAATGAAAAG | CAAACCTCGG | GGATACTGTC | 120
| TGATCATCAA | CAATCACAAT | TTTNCAAAAG | CACGGGAGAA | AGTGCCCAAA | CTTCACAGCA | 180
| TTAGGGACAG | GAATGGAACA | CACTTGGATG | CAGGG | | | 215

( 2 ) INFORMATION FOR SEQ ID NO:8:

(  i  ) SEQUENCE CHARACTERISTICS:
   ( A ) LENGTH: 332 base pairs
   ( B ) TYPE: nucleic acid
   ( C ) STRANDEDNESS: single
   ( D ) TOPOLOGY: linear ( i i ) MOLECULE TYPE: cDNA ( v i i ) IMMEDIATE SOURCE:
   ( A ) LIBRARY: TMLR2DT01
   ( B ) CLONE: 391083

( x i ) SEQUENCE DESCRIPTION: SEQ ID NO:8:

```
CTTGAACCTT GGGAATATTG AGATGGACTT CAGCAGAAAT CTTTATGATA TTGGGGAACA      60
ACTGGACAGT GAAGATCTGG CCTCCCTCAA GTTCCTGAGC CTGGACTACA TTCCGCAAAG     120
GAAGCAAGAA CCCATCAAGG ATGCCTTGAT GTTATTCCAG AGACTCCAGG AAAAGAGAAT     180
GTTGGAGGAA AGCAATCTGT CCTTCCTGAA GGAGCTGCTC TTCCGAATTA ATAGACTGGA     240
TTTGCTGATT ACCTACCTAA ACACTAGAAA GGAGGAGATG GAAAGGGAAC TTCAGACAAC     300
AGGCAGGGCT CAAATTTCTG CCTACAGGGT CA                                   332
```